United States Patent [19]

Shimenkov

[11] Patent Number: 4,805,646

[45] Date of Patent: Feb. 21, 1989

[54] TOOTHPICK

[76] Inventor: Marat Shimenkov, 65-46 Parsons Blvd., #2A, Flushing, N.Y. 11365

[21] Appl. No.: 77,449

[22] Filed: Jul. 24, 1987

[51] Int. Cl.[4] .......................................... A61C 15/00
[52] U.S. Cl. ................................... 132/329; 132/321; 433/89
[58] Field of Search ............... 132/89, 90, 93, DIG. 1, 132/84; D28/64

[56] References Cited

U.S. PATENT DOCUMENTS

| 516,409 | 3/1894 | Southwell | 132/89 |
| 656,479 | 8/1900 | Schellenbach | 132/89 |
| 710,498 | 10/1902 | McClain | 132/89 |
| 719,017 | 1/1903 | Lenhardtson | 132/89 |
| 4,397,327 | 8/1983 | Hadary | 132/90 |
| 4,570,653 | 2/1986 | Wolf | 132/89 |
| 4,577,649 | 3/1986 | Shimenkov | 132/89 |

FOREIGN PATENT DOCUMENTS 872511 7/1961 United Kingdom ................. 132/89

*Primary Examiner*—John Weiss
*Attorney, Agent, or Firm*—Ilya Zborovsky

[57] ABSTRACT

A toothpick has a body part with two body portions which are movable relative to one another to assume different angles. The toothpick can be filled with a substance which is then expelled by squeezing or displacing a part of it. Both ends of the toothpick can be formed as working ends with different sizes.

7 Claims, 2 Drawing Sheets

TOOTHPICK

BACKGROUND OF THE INVENTION

The present invention relates to toothpicks. More particularly it relates to such toothpicks which can be used for applying substances by the toothpick.

Toothpicks are widely known in the art. The known toothpicks have different shapes and sizes both of its working portion and its handle portion. It can be said that the known toothpicks have certain disadvantages in the way they treat respective surfaces to be cleaned, and also in their capability of introducing into a mouth respective substances. It is therefore believed to be clear that the known toothpicks can be further improved in this sense to provide more efficient and reliably action.

SUMMARY OF THE INVENTION

Accordingly, it is an object of the present invention to provide a toothpick which has certain improvements as compared with known toothpicks of this type.

In keeping with these objects and with others which will become apparent hereinafter, one feature of the present invention resides, briefly stated, in a toothpick which has a body part with at least two body portions movable relative to one another so as to assume different angles relative to one another.

Another feature of the present invention is that the toothpick can include a springy and elastic outer surface composed for example of two strips, and a soft and porous inner layer which can accommodate a substance to be squeezable out of it by squeezing the outer layer.

A further feature of the present invention is that the toothpick can have two opposite ends which are formed with different sizes, both in the longitudinal direction and in the transverse direction so as to act differently.

Still a further feature of the present invention is that at least an application portion of the toothpick can be covered by a cover which initially is reliably connected with the handle, and immediately before the use can be removed by breaking a connecting piece.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
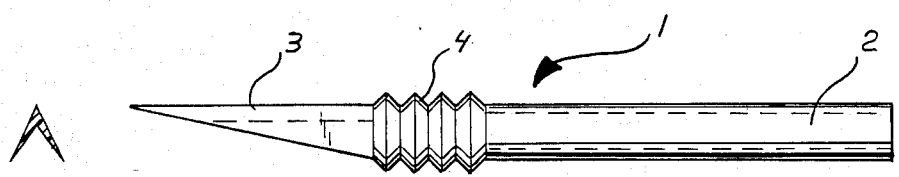
FIG. 1 is a view showing a toothpick in accordance with the present invention with a body part including two body portions movable relative to one another.

A toothpick in accordance with the present invention which is shown in FIG. 1 includes a body part which is identified as a whole with reference numeral 1. The body part has a handle portion 2 and a working portion 3. The handle portion 2 is connected with the working portion 3 so that they can be turned relative to one another so as to assume a plurality of different angles. This connection is performed by means of bellows 4 which connect the handle portion with the working portion. When the toothpick is formed so that the working portion can be turned relative to the handle portion, it is very easy to use it in the region of posterior teeth for cleaning. As can be seen from FIG. 1, the working portion 3, the bellows 4 and the handle portion 2 are all formed hollow. A substance in form of a paste, jello, syrup, can be introduced into the inner hollow of the toothpick. This substance can provide for cleaning, curing, antiseptic, deodorating, pain-relieving, freshening and other actions. For dispensing the substance from the toothpick into a respective area, the toothpick can be squeezed for example by squeezing the handle portion 2 which is for this purpose composed of an elastic material, for example of an elastic plastic. The same dispensing action can be performed by simply [turning]inserting the working portion between teeth [relative to thehandle portion 2], since during this [turning]insertion the bellows 4 is partially squeezed, its inner volume is reduced, and the substance is squeezed out from the inner space of the bellows as shown for example in FIG. 3.

Figure 2:
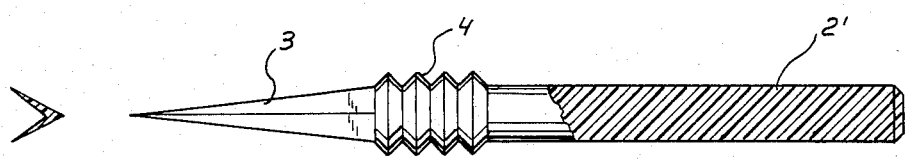
FIG. 2 is a view substantially corresponding to FIG. 1, but showing another embodiment of the toothpick of the present invention.
Figure 3:
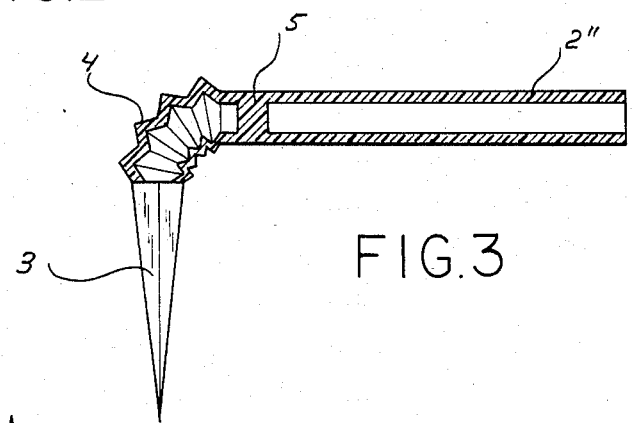
FIG. 3 is a view showing still a further embodiment of the toothpick of the present invention, wherein the body portions of the toothpick are turned relative to one another.

FIGS. 2 and 3 show further modifications of the toothpick of FIG. 1. In FIG. 2, a handle portion 2' is solid, while the working portion 3 and the bellows 4 are hollow. In FIG. 3 a part of the handle portion 2" is hollow and separated from the inner space of the bellows 4 by a partition 5.

In the embodiments of FIGS. 1, 2 and 3, the turning of the working portion relative to the handle portion is made possible by the provision of the bellows 4 therebetween. In the embodiments described hereinbelow, the turnability of the portions of the toothpick relative to one another is performed by means of different structural elements.

Figure 4:
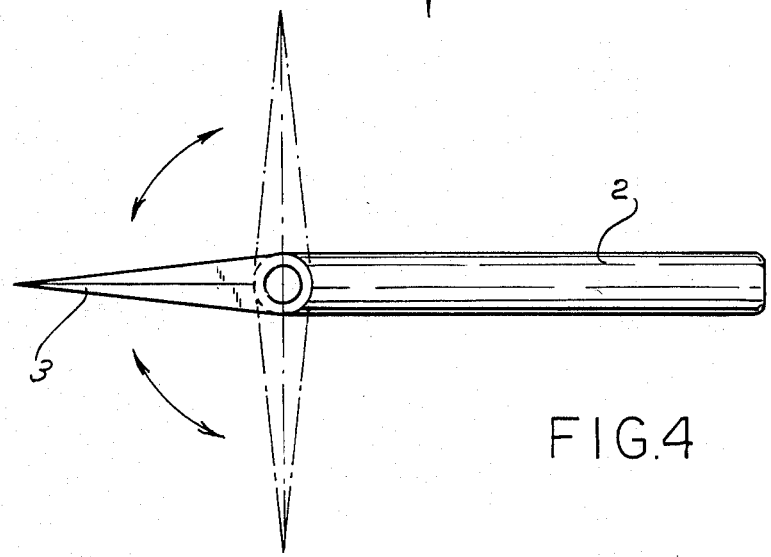
FIG. 4 is a view showing a further embodiment of the toothpick and particularly different means for movably connecting the body portions to one another.
Figure 5:
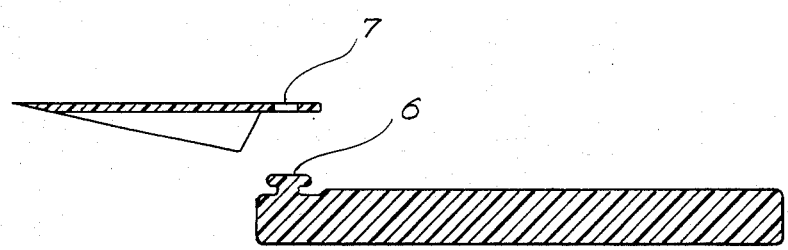
FIG. 5 is an exploded view of the toothpick in accordance with the embodiment shown in FIG. 4.

As shown in FIGS. 4 and 5, the handle portion 2 is connected with the working portion 3 by a hinge pin which includes a projection 6 formed in the handle portion 2 and a hole 7 formed in the working portion 3. The projection 6 pivotally engages in the hole 7. The user can turn the working portion 3 relative to the handle portion 2 about an axis of the hinge pin.

Figure 6:
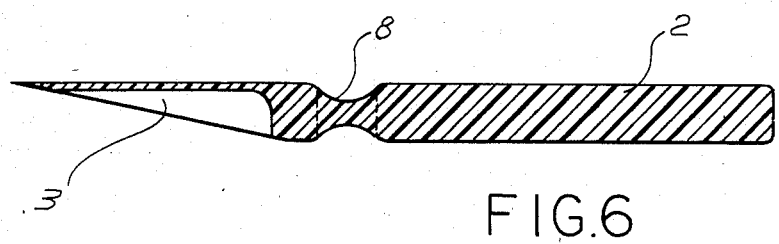
FIG. 6 is a view showing a still further possibility of forming the body portions of the toothpick movable relative to one another.
Figure 7:
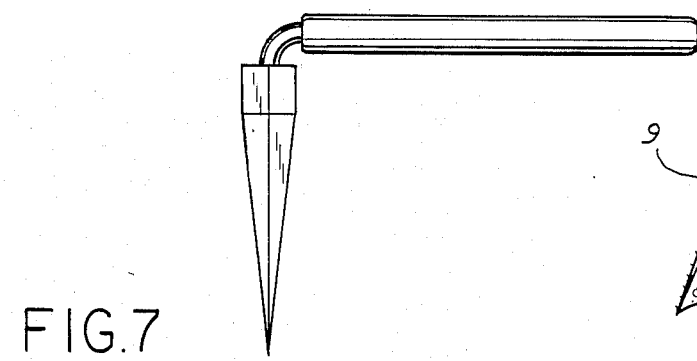
FIG. 7 is a view showing the toothpick of FIG. 6 in a position in which two body portions are turned relative to one another.

In the embodiment shown in FIGS. 6 and 7, the handle portion 3 and the working portion 3 are also turnable relative to one another. For this purpose, a constriction 8 is provided between these two portions and made of flexible material, for example, a flexible plastic. The user can turn the working portion 3 relative to the handle portion 2 with simultaneous bending of the constriction 8, as shown in FIG. 7.

The toothpick includes a working portion which is turnable relative to the handle portion; it can be introduced into a gap between the teeth in the region of posterior teeth of both gums from the buccal side, as well as from lingual side and palatal side.

Figure 8:
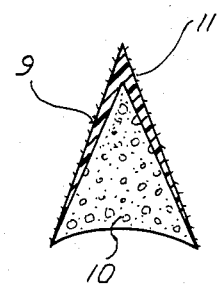
FIG. 8 shows a cross-section of the inventive toothpick in accordance with a special embodiment of the invention.
Figure 9:
FIG. 9 is a view showing the toothpick in accordance with an additional embodiment of the invention.

The toothpick shown in FIG. 8 has a triangular cross-section which is also true for the toothpicks of FIGS. 1-7. The triangular cross-section of the toothpick in FIG. 8 is achieved by the provision of two strips 9 which have free lower ends and upper ends connected with one another at the apex. The strips 9 are connected with one another elastically, for example they are formed of an elastic plastic. Thereby, during insertion of the working portion 3 into a gap between the teeth the strips 9 are somewhat squeezed and displaced toward one another so as to fit any gap between the teeth. In addition, an inner space between the strips 9 is filled by a porous material, for example, a porous plastic, and the pores of the porous material 10 can be saturated with a substance selected from the group described hereinabove. The material 10 can be attached to the strips 9 for example by glueing. During insertion the toothpick into a gap between the teeth and squeezing of the strips 9, the porous material 10 between the strips 9 is somewhat compressed and expels the substance from its pores so that the substance is dispensed into the respective areas. The elastic or springy nature of the strips 9 provides for a very firm abutment of the outer surfaces of the toothpick or its strips 9 against the respective surfaces of the adjacent teeth. The porous material also urges the strips away from one another and therefore further contributes to their abutment against the respective surfaces. Also the porous material manages by its lower surface an upper surface of portions between the teeth. In addition, an additional texture can be provided on the outer surfaces of the strips 9, for example in form of a nap 11, also of a plastic material. The nap additionally cleans the proximal surfaces of the adjacent teeth when the toothpick is introduced into a gap between the teeth.

As can be seen from FIG. 8, each strip has a cross-section which reduces toward the lower end and is pointed at the lower end. Therefore, when the toothpick is introduced in the tooth gap, the lower ends of the strips perform cleaning of pockets formed in the projection on a gum and the adjacent surface of a respective tooth.

Figure 10:
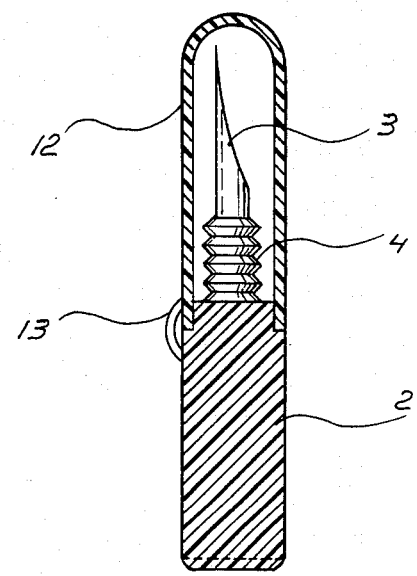
FIG. 10 is a view showing the toothpick in accordance with the present invention with a cover member which covers at least an application part.

A very important embodiment of the invention is shown in FIG. 10. Here, the toothpick is provided with a cover 12 which covers at least the application portion 3 so that it is retained in sterile condition. The cover 12 is connected with the handle portion 2 by a breakable piece 13. In normal condition, the cover 12 tightly closes the toothpick and surrounds the application part. Immediately before the use, the user removes the cover 12 with breaking of the piece 13, and exposes the application part to be introduced into respective areas of the mouth.

It will be understood that each of the elements described above, or two or more together, may also find a useful application in other types of constructions differing from the types described above.

While the invention has been illustrated and described as embodied in a toothpick, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A toothpick, comprising
a body part having at least two body portions which are movable relative to one another so as to assume at least two positions with at least two different angles relative to one another, and means for connecting said body portions with one another and including a hollow substance accommodating bellows which connects said body portions with one another and formed so that when one of said body portions is moved relative to the other of said body portions, a substance is squeezed from said bellows into one of said body portions.

2. A toothpick, comprising
a body part having at least two body portions which are movable relative to one another so as to assume at least two positions with at least two different angles relative to one another; and means for connecting said body portions with one another so as to allow the movement of said body portions relative to one another between said at least two positions, said body portions including a handle portion and a hollow substance accommodating application portion, and said connecting means including a hollow substance accommodating bellows which connects said body portions with one another, so as to apply by the toothpick a substance accommodated in said application portion and in said bellows.

3. A toothpick as defined in claim 2,; and further comprising a hood-like cover arranged to cover at least said application portion.

4. A toothpick as defined in claim 3, wherein said cover is connected with said handle portion by a breakable piece which can be broken by a user for removal of said cover from said application portion.

5. A toothpick, comprising
a body part having at least two body portions which are movable relative to one another so as to assume at least two positions with at least two different angles relative to one another, one of said body portions being formed, as two elongated strips each having a free end and an opposite end connected with an opposite end of the other of said strips; and a substance accommodating material located between said elongated strips and formed so that it can accommodate a substance and can be squeezed by displacing said strips toward one another with simultaneous dispensing the substance from said substance accommodating material.

6. A toothpick as defined in claim 5, wherein said strips are composed of a springy and elastic material, while said substance accommodating material is porous.

7. A toothpick as defined in claim 5, wherein said elongated strips have inner surfaces facing toward said substance accommodating material and outer surfaces provided with rough formations.

* * * * *